(12) United States Patent
Kyler et al.

(10) Patent No.: US 7,767,868 B2
(45) Date of Patent: Aug. 3, 2010

(54) PROCESS FOR PREPARING HIGH PURITY TNT

(75) Inventors: Keith S. Kyler, Kingsport, TN (US); Andrew R. Wilson, Kingsport, TN (US); Curtis Teague, Kingsport, TN (US)

(73) Assignee: BAE Ordnance Systems, Inc., Kingsport, TN (US)

( * ) Notice: Subject to any disclaimer, the term of this patent is extended or adjusted under 35 U.S.C. 154(b) by 372 days.

(21) Appl. No.: 10/553,825

(22) PCT Filed: Apr. 21, 2004

(86) PCT No.: PCT/US2004/012425

§ 371 (c)(1), (2), (4) Date: Feb. 28, 2008

(87) PCT Pub. No.: WO2005/005342

PCT Pub. Date: Jan. 20, 2005

(65) Prior Publication Data

US 2009/0312584 A1    Dec. 17, 2009

(51) Int. Cl.
*C07C 205/00* (2006.01)

(52) U.S. Cl. ..................................................... 568/932
(58) Field of Classification Search .................. 568/932
See application file for complete search history.

(56) References Cited

U.S. PATENT DOCUMENTS 5,616,818 A    4/1997    Pirkl et al.

OTHER PUBLICATIONS

Coon et al., aromatic nitration with nitric acid and trifluoromethane sulfonic acid, (Journal of Organic Chemistry (1973), 38 (25), 4243-4248.*

* cited by examiner

*Primary Examiner*—Jafar Parsa
(74) *Attorney, Agent, or Firm*—Daniel J. Long

(57) ABSTRACT

A process for preparing trinitrotoluene (TNT) in which toluene is treated with nitric acid having a concentration of about 90% to about 99%, and preferably about 98% to about 99%, by weight at a temperature of less than about 60° C., and preferably less than 30° C., to produce high purity dinitrotoluene. The resulting dinitrotoluene is then treated with nitric acid having a concentration of about 98% to about 99% by weight and trifluoromethane sulfuric acid to produce high purity TNT.

9 Claims, No Drawings

PROCESS FOR PREPARING HIGH PURITY TNT

BACKGROUND OF THE INVENTION

1. Field of the Invention

The present invention relates to organic chemistry and more particularly to the processing of aromatic hydrocarbons. Still more particularly, the present invention relates to processes for preparing trinitrotoluene (TNT).

2. Brief Description of Prior Developments

In the prior art process of preparing TNT, one mole of 2,4-dinitrotoluene is added to a mixture of 3 moles of concentrated nitric acid and 5 moles of concentrated sulfuric acid. The mixture is heated to 130° C. for 2 hours. The dark red brown viscous solution is poured into a large volume of water and the crude TNT product is isolated by filtration, then purified by washing with sodium sulfite solution which affords a "red water" waste containing TNT isomers and impurities. The TNT is then washed with hot water. The yield of TNT is approximately 84%

A disadvantage of this prior art process is due to the fact that a large volume of concentrated sulfuric acid is used. The acid mixture is highly corrosive. The initial crude TNT is impure and must be purified by sulfite washing which produces a environmentally hazardous waste. The resulting large volume of spent sulfuric acid must be recovered and purified for reuse.

SUMMARY OF INVENTION

An object of the present invention is to overcome the limitations of the prior art methods requiring large quantities of strong oxidizing acids such as sulfuric acid while maintaining an economically useful process.

Another object of the present invention is to avoid producing the environmentally hazardous "red water" waste stream which is created with other methods.

In the process of the present invention, TNT is prepared in high purity by either a two step process beginning with toluene or alternatively a one step process starting with dinitrotoluene.

Toluene reacts with 90-99% nitric acid and preferably 98-99% nitric acid at <60° C. and preferably <30° C. to afford a high yield of high purity dinitrotoluene (DNT) at a purity of 99% by weight. The DNT which can be readily converted to TNT by heating this material with a mixture of 98-99% nitric acid in the presence of only one equivalent of the non-oxidizing acid, trifluoromethanesulfonic acid. The process affords very high purity TNT having a purity of >99% by weight. Unless otherwise stated, all concentrations herein are by weight.

DETAILED DESCRIPTION OF THE PRESENT INVENTION

In the present invention TNT is prepared from toluene or 2,4-dinitrotoluene by the following reactions.

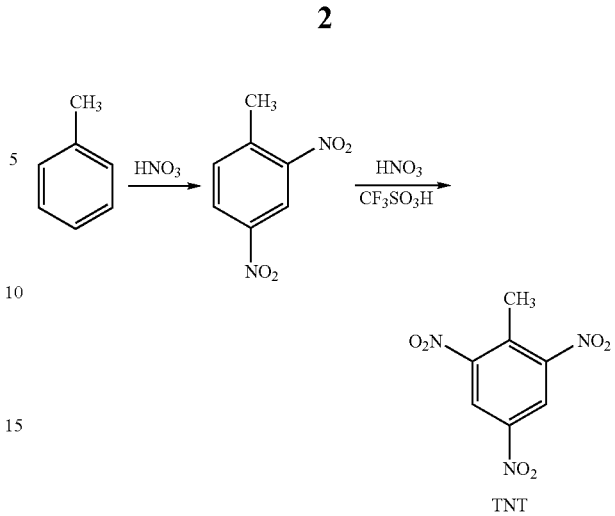

The invention is further described with reference to the following example:

Example

The following materials were used: 98% $HNO_3$; toluene purchased from Burdick Jackson; and trifluoromethanesulfonic acid purchased from Acros, cat. #169890-500, lot#A016403801.

The process was carried out as follows:

1. A 2 L reactor was charged with 504 mL (8 mol) of 98% nitric acid. The acid was cooled to an internal temperature of 5° C. (external jacket temperature set at 0° C.).
2. Then 214 mL (2 mol) toluene was added dropwise using an addition funnel at a rate to maintain the internal temperature below 30° C. The addition took about 45-50 mins. The reaction was extremely exothermic with each drop of toluene producing a transient orange-brown color which disappeared quickly. Only small amounts of NOx fumes were observed.
3. After complete addition of toluene, the homogeneous mixture was warmed to room temperature and the excess nitric acid and water were removed by distillation under a mild vacuum (50 mmHg) with an external jacket temperature of 105° C.
4. The distillation was continued until all the nitric acid and water stopped distilling (required about 30 min), then the molten DNT was maintained under vacuum at 105° C. for an addition 30 min.
5. This material was not isolated but was used for subsequent conversion to TNT. After drying at 105° C. for 30 min, the molten DNT was cooled to 50° C. prior to the addition of the next reagents.
6. The following describes the conversion of DNT to TNT.
7. A solution was prepared in a 2 L Erlenmeyer flask by adding, over a 5 min period, 300 grams, 188 mL (2 mol) of trifluoromethanesulfonic acid (triflic acid) to 1210 mL (20 mol) of 98% nitric acid. There was a slight warming of the solution during the addition of the triflic acid and the mixture warmed to about 50° C.
8. This solution was then added in one portion to the cooled DNT in the 2 L reactor.
9. The homogeneous orange solution was then heated to reflux and the progress of the reaction may be monitored by thin layer chromatography.

10. An external jacket temperature of 110° C. was used for heating and the internal temperature rose slowly from 85° C. to about 92° C. during the course of the reaction.
11. Various nitric oxide fumes were observed and were adequately vented throughout the reaction.
12. The mixture was heated for a total of 4 hrs.
13. Then the excess nitric acid was removed by distillation under a medium vacuum of about 50 mmHg distillation at a temperature of 85° C.
14. When the nitric acid was finished distilling, the molten TNT separated as a yellow oil on top of the triflic acid/water layer.
15. The reactor was cooled to room temperature with vigorous agitation until the TNT crystallized as pale yellowish white needles.
16. Then 1 L of water was added and the crystalline TNT was collected by suction filtration on a sintered-glass funnel.
17. The TNT was further washed with an addition of 2 L of water, and the product was dried by sucking air through the crystals in the funnel until all of the surface water has been thoroughly removed.
18. The product was then dried in an oven for 48 hrs.
19. The yield of TNT was 415 grams, 91%.
20. Analysis of the product showed the purity was >99%.

It will be appreciated that the process of this invention eliminates the use of sulfuric acid by using a less caustic and less oxidizing acid, namely trifluoromethanesulfonic acid (triflic acid). Less acid, only one molar equivalent, is required in the new method, and the temperature of the reaction is lower (85-90° C.). A higher purity TNT product is obtained eliminating the sulfite washing stage thus eliminating the hazardous "red water" waste stream.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A process for preparing trinitrotoluene (TNT) comprising the steps of:
    (a) at a temperature of less than about 60° C. treating toluene with nitric acid having a concentration of from about 90% to about 99% by weight to produce dinitrotoluene (DNT), such that the DNT is produced at a purity greater than about 98% by weight; and
    (b) then treating the DNT formed in step (b) with nitric acid having a concentration of from about 98% to about 99% by weight and about one molar equivalent of trifluoromethanesulfonic acid to produce the TNT, such that the TNT is produced at a purity greater than about 98% by weight and without the need to use sulfuric acid.

2. The process of claim 1 wherein in step (a) the nitric acid has a concentration of from about 98% to about 99% by weight.

3. The process of claim 1 wherein step (a) is carried out at a temperature of less than about 30° C.

4. The process of claim 1 wherein in step (a) the DNT is produced at purity of greater than about 99% by weight.

5. The process of claim 1 wherein in step (b) the TNT is produced at a purity greater than about 99% by weight.

6. A process for preparing trinitrotoluene (TNT) from dinitrotoluene (DNT) comprising the step of:
    treating the DNT with nitric acid having a concentration of from about 98% to about 99% by weight and about one molar equivalent of trifluoromethanesulfonic acid to produce TNT, wherein the TNT is produced at a purity greater than about 98% by weight and without the need to use sulfuric acid.

7. The process of claim 6 wherein the DNT has a purity of greater than about 98% by weight.

8. The process of claim 7 wherein the DNT has a purity of greater than about 99% by weight.

9. The process of claim 6 wherein the TNT is produced at a purity greater than about 99% by weight.

* * * * *